United States Patent [19]

Priddy

[11] 4,052,464

[45] Oct. 4, 1977

[54] PROCESS FOR THE MANUFACTURE OF DI-T-BUTYLPEROXY KETALS

[75] Inventor: Duane B. Priddy, Coleman, Mich.

[73] Assignee: The Dow Chemical Company, Midland, Mich.

[21] Appl. No.: 597,792

[22] Filed: July 21, 1975

[51] Int. Cl.$^2$ ............................................. C07C 179/06
[52] U.S. Cl. .......................... 260/610 C; 260/610 SK; 260/610 R
[58] Field of Search ........... 260/610 R, 610 C, 610 D, 260/610 A, 610 SK

[56] References Cited

U.S. PATENT DOCUMENTS

| | | | |
|---|---|---|---|
| 2,455,569 | 12/1948 | Dickey | 260/610 C |
| 2,537,853 | 1/1951 | Pezzaglia | 260/610 C |
| 3,308,163 | 3/1967 | McKellin | 260/610 C |
| 3,472,901 | 10/1969 | Tijssen et al. | 260/610 R |

*Primary Examiner*—James O. Thomas, Jr.
*Assistant Examiner*—W. B. Lone
*Attorney, Agent, or Firm*—R. B. Ingraham

[57] ABSTRACT

Di-t-butylperoxy ketals are prepared from t-butyl hydroperoxide and the appropriate ketone in the presence of from 1 to 10 times the weight of ketone of ethylbenzene employing an acidic catalyst. Water is removed by azeotropic distillation with ethylbenzene and excess t-butyl hydroperoxide is subsequently removed by azeotropic distillation of additional ethylbenzene to provide a solution of the di-t-butylperoxide ketal in ethylbenzene which is particularly desirable as an initiator for styrene polymerization.

3 Claims, No Drawings

PROCESS FOR THE MANUFACTURE OF DI-T-BUTYLPEROXY KETALS

Di-t-butylperoxide ketals are desirable polymerization initiators for the preparation of certain vinyl addition polymers such as polystyrene, copolymers of styrene with other olefinically unsaturated monomers such as methyl methacrylate, acrylonitrile, butadiene, α-methyl styrene and the like, either alone or in the presence of a reinforcing agent such as a rubber, most often a polybutadiene rubber or a butadiene-styrene rubber. Oftentimes in the preparation of styrene polymers and copolymers, the polymerization is conducted in the absence of water in a bulk or solution polymerization process wherein free radical initiation occurs in the oil phase as contrasted to emulsion polymerization where free radical initiation occurs primarily in the aqueous phase. In the mass or bulk polymerization of a so-called mass suspension polymerization, all of the monomer is not converted to polymer and for convenience of processing of the polymerizing mixture, a small quantity of solvent, both for monomer and polymer is employed. Beneficially, such solvent is generally employed at levels from about 5 to 50 percent by weight of the process mixture and beneficially at levels from about 5 to 20 weight percent of the contents of the reactor. Peroxides, particularly the di-t-butylperoxy ketals exhibit a significant tendency to decompose on heating or on exposure to mechanical shock. Thus, it is very undesirable to transport or handle di-t-butylperoxy ketals in a dry condition. It is preferred to handle such compounds in the form of a solution.

It would be desirable if there were available an improved process for the preparation of di-t-butylperoxy ketals which provided a product particularly suitable for the polymerization of styrene polymers and copolymers.

It would also be desirable if there were available an improved process for the preparation of di-t-butylperoxy ketals which was rapid and did not require the isolation of the di-t-butylperoxy ketals from at least a portion of the original reaction mixture.

It would also be desirable if there were available an improved method for the preparation of di-t-butylperoxy ketals, in a form particularly suitable for use of the preparation of styrene containing polymers.

These benefits and other advantages in accordance with the present invention are achieved in a method for the preparation of di-t-butylperoxy ketals from a ketone and tertiarybutyl hydroperoxide in the presence of an acidic catalyst wherein the ketone and tertiarybutyl hydroperoxide and acidic catalyst are dispersed in a solvent at a temperature below the decomposition temperature of the desired di-t-butylperoxy ketals and under a pressure sufficiently low that water is removed from the reaction mixture and condensed at a location remote from the reaction mixture to thereby convert at least a major portion of the ketone to the corresponding di-t-butylperoxy ketals, the improvement which comprises employing as a solvent ethylbenzene conducting the reaction in the presence of an excess of tertiarybutyl hydroperoxide removing water from the reaction by azeotropic distillation with ethylbenzene and removing at least a major portion of the excess tertiarybutyl hydroperoxide by azeotropic distillation with the ethylbenzene to provide a solution containing at least one di-t-butylperoxy ketal and ethylbenzene.

The method of the present invention can be readily practiced for the preparation of all di-t-butylperoxy ketals which are soluble in ethylbenzene. Generally the di-t-butylperoxy ketals which are most soluble in ethylbenzene are those compounds which contain primarily carbon, hydrogen, and the principal oxygen content being in the tertiarybutylperoxy groups.

Generally in the practice of the present invention, it is desirable to conduct the reaction at a temperature of about 30° to 80° C and beneficially from a temperature of about 40° to about 65° C. Below 30° C, the reaction rate becomes undesirably slow and above 80° C there is a tendency for the di-t-butylperoxy ketals to decompose. Generally it is desirable to conduct the reaction under a pressure of from 20 to 100 millimeters of Mercury, in order to remove the water, ethylbenzene azeotrope and the ethylbenzene tertiarybutylperoxide azeotrope at a convenient rate. Usually in practice of the present invention it is desirable to employ from $2\frac{1}{2}$ to 4 moles of the tertiarybutyl hydroperoxide per mole of the ketone and acidic catalyst such as sulfuric acid, para-toluene sulfonic acid, phosphoric acid, dodecylbenzenesulfonic acid, dodecylphosphoric acid, oxalic acid, acidic ion exchange resin, acidic molecular sieves or acidic clays. All known acidic catalysts which promote the addition of tertiarybutylhydroperoxide to a ketone group to form th di-t-butylperoxy ketals may be employed in the practice of the present invention. Ethylbenzene is employed in a quantity of from about 1 to 10 times the weight of the ketone and optionally a nonvolatile or high boiling diluent may be employed in a proportion of $\frac{1}{2}$ to 3 times the weight of the ketone.

The process of the present invention may be carried out in a batch process or continuous process or partially batch, partially continuous process. The formation of the di-t-butylperoxy ketals may be carried out batchwise and the ethylbenzene tertiarybutylhydroperoxide azeotrope removed continuously by passing the reaction mixture continuously through a distillation apparatus such as a falling film still or alternatively the reaction is readily carried out in a falling film distillation apparatus. The acidic catalyst may be introduced to the still column with the feed or an insoluble acidic surface or bed within the still may be utilized.

Generally it is desirable in the azeotropic distillation of the water-ethylbenzene mixture to separate the water and ethylbenzene external to the reactor and return the ethylbenzene to the reaction mixture. When the tertiarybutylhydroperoxide-ethylbenzene azeotrope is being removed, it is desirable that none of this material be returned to the reactor, as the tertiarybutylhydroperoxide is soluble in the ethylbenzene. In most instances, the amount of tertiarybutylhydroperoxide remaining in the product solution is usually less than one-half of 1 percent. Ethylbenzene contaminated with residual tertiarybutylhydroperoxide is quite satisfactory for use in the process of the invention. The ethylbenzene tertiarybutylhydroperoxide azeotrope contains about 27 weight percent peroxide and is not shock sensitive.

The present invention is illustrative but not limited by the following examples.

EXAMPLE I

A two hundred gallon stirred reactor fitted with a reflux condenser having a water trap is charged with 80 pounds of cyclohexanone, 200 pounds of mineral oil, 800 pounds ethylbenzene, and 313 pounds of a solution of 70 weight percent tertiarybutylhydroperoxide in water. The mixture was agitated in the reactor for 10 minutes and allowed to stand for an additional 10 minutes. Forty-five pounds of water were drained from the bottom of the reactor. The contents of the reactor were then placed under an absolute pressure of 90 millimeters of Mercury and the contents of the reactor heated to 50° as water was continuously removed by azeotropic distillation with ethylbenzene. When the temperature of the contents reached 50° C, 300 grams of paratoluenesulfonic acid was added. The reactor temperature was increased to 60° C and maintained at 60° C until no more water was being removed by azeotropic distillation. This required a period of about 30 minutes. Azeotropic distillation was continued removing unreacted tertiarybutylhydroperoxide until 590 pounds of distillate was removed. The remaining reaction product was filtered through a bed of anhydrous particulate sodium carbonate. The total weight of material removed from the reactor through the bed was 740 pounds. The ethylbenzene azeotrope removed was analyzed by gas chromatography and found to contain 12 weight percent tertiarybutylhydroperoxide, and the filtered solution was analyzed by gas chromatography and indicated to be 25 weight percent 1,1-bis(tertiarybutylperoxy)cyclohexanone, 0.2 weight percent tertiarybutylhydroperoxide, 0.4 weight percent cyclohexanone and the remaining 74.4 percent was assumed to be ethylbenzene and mineral oil. The filtered solution was tested for shock sensitivity employing an apparatus and procedure developed by joint Army, Navy, Air Force Panel on Liquid Propellant Test Methods, no decomposition was observed. When the same test was applied to pure 1,1-bis(tertiarybutylperoxy)cyclohexanone, decomposition is observed at the lowest shock level which can be delivered by the apparatus.

A solution consisting of one percent by weight tertiarybutylhydroperoxide in ethylbenzene was distilled through a 2-inch diameter, 24-inch long glass distillation column packed with ¼-inch Berl saddles at a 3 to 1 reflux ratio under a pressure of 50 millimeters of mercury. The finished fraction of condensate collected at a boiling point of 49° C and contained 27.2 percent by weight of tertiarybutylhydroperoxide as determined by iodiometric titration.

EXAMPLE II

The reactor employed in Example I was charged with 63 pounds of 4-tertiarybutyl cyclohexanone, 540 pounds of ethylbenzene, and 170 pounds of an aqueous solution of tertiarybutylhydroperoxide which contained 70 weight percent tertiarybutylhydroperoxide. The contents of the reactor were agitated for a period of 10 minutes and then permitted to stand for a period of 10 minutes. Twenty pounds of water were drained from the bottom of the reactor. The contents of the reactor were heated to a temperature of 50° C under a pressure of 90 millimeters of mercury and water removed from the reactor by azeotropic distillation with ethylbenzene. The ethylbenzene external to the reactor was separated from the water and returned to the reactor. When it appeared that no additional water could be removed by azeotropic distillation, the contents of the reactor were cooled to 25° C and 80 grams of paratoluenesulfonic acid were added. The contents of the reactor were again heated to 55° C and water continually removed by azeotropic distillation with ethylbenzene. When water was no longer being removed from the reactor, the ethylbenzene tertiary-butylhydroperoxide azeotrope was then removed until 232 pounds of distillate were collected. The contents of the reactor were then cooled to 25° C and passed through a particulate bed of sodium carbonate. Analysis of the ethylbenzene tertiarybutylhydroperoxide azeotrope by iodimetric titration indicated that the distillate was about 20 weight percent tertiarybutylhydroperoxide. Four hundred and seventy two pounds of reaction mixture were recovered from the reactor and analysis by iodimetric titration showed that the mixture contained 18 weight percent of 1,1-bis(tertiarybutylperoxy)-4-tertiarybutylcyclohexanone.

EXAMPLE III

A half-liter flask fitted with a condenser and water trap was charged with 20 grams of methylisobutylketone, 78 grams of 70 weight percent aqueous solution of tertiarybutylhydroperoxide and 100 grams of ethylbenzene. The pressure on the flask was reduced from atmospheric pressure to 90 millimeters of mercury and the contents of the flask heated to about 50° C. Water was removed by azeotropic distillation with ethylbenzene. When no additional water appeared, 5 grams of anhydrous oxalic acid and additional water was removed from the mixture over a period of 2 hours. When all water had apparently been removed, an additional 100 grams of ethylbenzene was added to the flask and 106 grams of tertiarybutylhydroperoxide ethylbenzene azeotrope distilled from the mixture. The pot temperature during the distillation varied from about 48° to 50° and the head temperature of the distillation column rose from 39° to 48°. The column employed was a 4 ft. by 1 in. Vigreaux column; a 3 to 1 reflux ratio was maintained. The distillate was analyzed by gas chromatography and contained 19 weight percent tertiarybutylhydroperoxide, 1 weight percent methylisobutylketone and 80 weight percent ethylbenzene. The contents of the flask were filtered to remove the oxalic acid, the filtrate was a clear water white solution weighing 145 grams. Iodimetric titration of a portion of the filtrate indicated that it contained 31 weight percent of 2,2-bis(tertiarybutylperoxy)-4-methylpentane to provide a yield of 80 percent.

EXAMPLE IV

The apparatus of Example III was charged with 13 grams of ethyl acetoacetate, 78 grams of a 70 weight percent tertiarybutylhydroperoxide aqueous solution, 30 grams of mineral oil and 60 grams of ethylbenzene. The pressure in the flask was reduced to 90 millimeters of mercury and water removed from the flask by azeotropic distillation with ethylbenzene. The ethylbenzene was returned to the flask after being separated from the water. After about an hour, no additional water was being removed from the flask, 0.13 grams of paratoluene sulfonic acid was added and water again removed from the mixture by azeotropic distillation with ethylbenzene. When the evolution of water from the reaction mixture appeared complete, 10 grams of cyclohexanone, 20 grams of mineral oil, and an additional 20 grams of ethylbenzene followed by 0.1 grams of paratoluene sulfonic acid were added to the flask. Water was again removed from the reaction mixture by azeotropic distillation. After a period of about 30 minutes the evolution of water stopped and 2 grams of anhydrous sodium acetate were added to neutralize the paratoluene sulfonic acid. A stream of nitrogen was applied to the reaction mixture until it had been reduced in weight to 110 grams. The reaction mixture was then filtered to remove solids. The filter reaction mixture was then analyzed and the following results obtained:

21 weight percent 1,1-bis(tertiarybutylperoxy)cyclohexanone, 24 weight percent ethyl-3,3-bis(tertiarybutylperoxy)butrate, 47 weight percent mineral oil, 7 weight percent ethylbenzene, less than 1 percent tertiarybutylperoxide, less than ½ percent ethylacetoacetate, less than 0.2 weight percent cyclohexanone. The yield of 1,1-bis(tertiarybutylperoxy)cyclohexane was 89 percent and that of ethyl-3,3-bis(tertiarybutylperoxy)butrate was 91 percent.

In a manner similar to the foregoing procedures, other di-t-butylperoxy ketals are readily prepared.

When 2,2-bis(4-ketocyclohexyl)propane is employed 2,2-bis(4,4-di-t-butylperoxycyclohexyl)propane is obtained.

When 4-octylcyclohexanone is employed 1,1-bis(t-butylperoxy)-4-octylcyclohexane is obtained.

When 5-methyl-2-hexanone is employed 2,2-bis(t-butylperoxy)-5-methylhexane is obtained.

When 3,3,5-trimethylcyclohexanone is employed 1,1-bis(t-butylperoxy)-3,3,5-trimethylcyclohexanone is obtained.

When 2-butanone is employed 2,2-bis(t-butylperoxy)butane is obtained.

When 2-hexanone is employed 2,2-bis(t-butylperoxy)hexane is obtained.

When 2-octanone is employed 2,2-bis(t-butylperoxy)octane is obtained.

When methyl acetoacetate is employed methyl-3,3-bis(t-butylperoxy)butyrate is obtained.

When propyl acetoacetate is employed propyl-3,3-bis(t-butylperoxy)butyrate is obtained.

When butyl acetoacetate is employed butyl-3,3-bis(t-butylperoxy)butyrate is obtained.

When ethyl levulate is employed ethyl-4,4-bis(t-butylperoxy)valerate is obtained.

When butyl levulate is employed butyl-4,4-bis(5-butylperoxy)valerate is obtained.

In a manner similar to the foregoing, a wide variety of di-t-butylperoxy ketals are readily prepared in solution employing ethylbenzene to azeotropically remove both water and excess tertiarybutylhydroperoxide from the reaction mixture.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

What is claimed is:

1. In a method for the preparation of ethylbenzene soluble di-t-butylperoxy ketals from a ketone and tertiarybutyl hydroperoxide in the presence of an acidic catalyst wherein the ketone and tertiarybutyl hydroperoxide in a molar ratio of 1:2½ to 1:4 and acidic catalyst such as sulfuric acid, para-toluene sulfonic acid, phosphoric acid, dodecylbenzenesulfonic acid, dodecylphosphoric acid, oxalic acid are dispersed in a solvent at a temperature 30°–80° C below the decomposition temperature of the desired di-t-butylperoxy ketals and under a pressure from 20 to 100 millimeters mercury, a pressure sufficiently low that water is removed from the reaction mixture and condensed at a location remote from the reaction mixture to thereby convert at least a major portion of the ketone to the corresponding di-t-butylperoxy ketals, the improvement which comprises employing ethylbenzene in proportions of about 1 to 10 times by weight of the ketone as the solvent conducting the reaction in the presence of an excess of tertiarybutyl hydroperoxide, removing water from the reaction mixture by azeotropic distillation with ethylbenzene and removing at least a major portion of the excess tertiarybutyl hydroperoxide by azeotropic distillation with ethylbenzene to provide a solution containing at least one di-t-butylperoxy ketal and ethylbenzene.

2. The method of claim 1 wherein an inert liquid diluent is included, the diluent having a boiling point greater than ethylbenzene.

3. The method of claim 2 wherein the diluent is mineral oil.

* * * * *